US008101820B2

(12) United States Patent
Ishida et al.

(10) Patent No.: US 8,101,820 B2
(45) Date of Patent: Jan. 24, 2012

(54) METHOD FOR INCREASING TRANSFORMATION EFFICIENCY IN PLANTS, COMPRISING COCULTURE STEP FOR CULTURING PLANT TISSUE WITH COCULTURE MEDIUM CONTAINING 3,6-DICHLORO-O-ANISIC ACID

(75) Inventors: Yuji Ishida, Iwata (JP); Yukoh Hiei, Iwata (JP)

(73) Assignee: Japan Tobacco Inc., Tokyo (JP)

( * ) Notice: Subject to any disclaimer, the term of this patent is extended or adjusted under 35 U.S.C. 154(b) by 0 days.

(21) Appl. No.: 12/528,965

(22) PCT Filed: Feb. 28, 2008

(86) PCT No.: PCT/JP2008/053558
§ 371 (c)(1),
(2), (4) Date: Oct. 29, 2009

(87) PCT Pub. No.: WO2008/105508
PCT Pub. Date: Sep. 4, 2008

(65) Prior Publication Data
US 2010/0068812 A1    Mar. 18, 2010

(30) Foreign Application Priority Data

Feb. 28, 2007 (JP) ................................. 2007-049161

(51) Int. Cl.
*C12N 15/82* (2006.01)
*C12N 15/87* (2006.01)
(52) U.S. Cl. ...................................................... 800/278
(58) Field of Classification Search .................. 800/278, 800/298, 300, 312; 435/4, 415; 536/23.2, 536/23.7
See application file for complete search history.

(56) References Cited

U.S. PATENT DOCUMENTS 7,851,670 B2 * 12/2010 Wan et al. ..................... 800/278

FOREIGN PATENT DOCUMENTS

| EP | 1 306 441 A1 | 5/2003 |
|---|---|---|
| EP | 1662002 A1 | 5/2006 |
| EP | 1669444 A1 | 6/2006 |
| JP | 2000-23675 A | 1/2000 |
| JP | 2000-342253 A | 12/2000 |
| JP | 2000-342255 A | 12/2000 |
| JP | 2000-342256 A | 12/2000 |
| WO | WO 02/12520 A1 | 2/2002 |
| WO | WO 02/12521 A1 | 2/2002 |
| WO | WO 2005/017152 A1 | 2/2005 |
| WO | WO 2005/017169 A1 | 2/2005 |

OTHER PUBLICATIONS

Chan, M-T. et al. "*Agrobacterium*-mediated production of transgenic rice plants expressing a chimeric α-amylase promoter/β-glucuronidase gene," Plant Molecular Biology, vol. 22, pp. 491-506, 1993.

Cheng, M. et al., "Genetic Transformation of Wheat Mediated by *Agrobacterium tumefaciens*," Plant Physiol., vol. 115, pp. 971-980, 1997.
Chih-Ching, C., "The N6 Medium and Its Applications to Anther Culture of Cereal Crops," Plant Tissue Culture, Pittman Publishing Limited, London, pp. 43-50, 1978.
De Cleene, M. et al., "The Host Range of Crown Gall," The Botanical Review, vol. 42, No. 4, pp. 389-466, Oct.-Dec. 1976.
Deji, A. et al., "Genomic organization and transcriptional regulation of maize ZmRR1 and ZmRR2 encoding cytokinin-inducible response regulators," Biochimica et Biophysica Acta, vol. 1492, pp. 216-220, 2000.
Duncan, D.R. et al., "The production of callus capable of plant regeneration from immature embryos of numerous *Zea mays* genotypes," Planta, vol. 165, pp. 322-332, 1985.
Frame, B.R. et al., "*Agrobacterium tumefaciens*-Mediated Transformation of Maize Embryos Using a Standard Binary Vector System," Plant Physiol., vol. 129, pp. 13-22, May 2002.
Gould, J. et al. "Transformation of *Zea mays* L. Using *Agrobacterium tumefaciens* and the Shoot Apex," Plant Physiol., vol. 95, pp. 426-434, 1991.
Grimsley, N. et al. "DNA transfer from *Agrobacterium* to *Zea mays* or *Brassica* by agroinfection is dependent on bacterial virulence functions," Mol. Gen. Genet., vol. 217, pp. 309-316, 1989.
Grimsley, N. et al., "*Agrobacterium*-mediated delivery of infectious maize streak virus into maize plants," Nature, vol. 325, pp. 177-179, Jan. 8, 1987.
Grimsley, N.H. et al., "Meristematic Tissues of Maize Plants are Most Susceptible to Agroinfection With Maize Streak Virus," Bio/technology, vol. 6, pp. 185-189, Feb. 1988.
Hiei, Y. et al., "Efficient transformation of rice (*Oryza sativa* L.) mediated by *Agrobacterium* and sequence analysis of the boundaries of the T-DNA," The Plant Journal, vol. 6, No. 2, pp. 271-282, 1994.
Huang, X. et al., "Successful *Agrobacterium*-mediated genetic transformation of maize elite inbred lines," Plant Cell, Tissue and Organ Culture, vol. 83, pp. 187-200, 2005.
International Search Report dated Apr. 1, 2008, for Application No. PCT/JP2008/053558.
Ishida, Y. et al, "High efficiency transformation of maize (*Zea mays* L.) mediated by *Agrobacterium tumefaciens*," Nature Biotechnology, vol. 14, pp. 745-750, Jun. 1996.
Ishida, Y. et al., "Improved Protocol for Transformation of Maize (*Zea mays* L.) Mediated by *Agrobacterium tumefaciens*," Plant Biotechnology, vol. 20, No. 1, pp. 57-66, 2003.
Komari, T. et al. "Efficient selection of somatic hybrids in *Nicotiana tabacum* L. using a combination of drug-resistance markers introduced by transformation," Theor. Appl. Genet., vol. 77, pp. 547-552, 1989.
Komari, T. et al., "Vectors carrying two separate T-DNAs for co-transformation of higher plants mediated by *Agrobacterium tumefaciens* and segregation of transformants free from selection markers," The Plant Journal, vol. 10, No. 1, pp. 165-174, 1996.

(Continued)

*Primary Examiner* — Kent L Bell
(74) *Attorney, Agent, or Firm* — Birch, Stewart, Kolasch & Birch, LLP

(57) ABSTRACT

The present invention aims to provide a method for increasing transformation efficiency in plants when compared to conventionally known *Agrobacterium*-mediated methods.
In the present invention, one of the features is to comprise a coculture step for culturing an *Agrobacterium*-inoculated plant tissue with a coculture medium containing 3,6-dichloro-o-anisic acid.

6 Claims, 3 Drawing Sheets

OTHER PUBLICATIONS

Linsmaier, E. et al., "Organic Growth Factor Requirements of Tobacco Tissue Cultures," Physiol. Plant., vol. 18, pp. 100-127, 1965.

Mooney, P.A. et al., "*Agrobacterium tumefaciens*-gene transfer into wheat tissues," Plant Cell, Tissue and Organ Culture, vol. 25, pp. 209-218, 1991.

Negrotto, D. et al., "The use of phosphomannose-isomerase as a selectable marker to recover transgenic maize plants (*Zea mays* L.) via *Agrobacterium* transformation," Plant Cell Reports, vol. 19, pp. 798-803, 2000.

Nomura, M. et al., "The evolution of C4 plants: acquisition of cis-regulatory sequences in the promoter of C4-type pyruvate, orthophosphate dikinase gene," Plant J., vol. 22, No. 3, pp. 211-221, 2000.

Nomura, M. et al., "The promoter of rbcS in a C3 plant (rice) directs organ-specific, light-dependent expression in a C4 plant (maize), but does not confer bundle sheath cell-specific expression," Plant Mol. Biol., vol. 44, pp. 99-106, 2000.

Potrykus, I., "Gene Transfer to Cereals: An Assessment," Bio/Technology, vol. 8, pp. 535-542, Jun. 1990.

Raineri, D.M. et al., "*Agrobacterium*-Mediated Transformation of Rice (*Oryza Sativa* L.)," Bio/Technology, vol. 8, pp. 33-38, Jan. 1990.

Sambrook, J. et al., Molecular Cloning: A Laboratory Manual, Second Edition, Cold Spring Harbor Laboratory Press, Cold Spring Harbor, New York, pp. 9.31-9.62, 1989.

Taniguchi, M. et al. "The Promoter for the Maize C4 Pyruvate, Orthophosphate Dikinase Gene Directs Cell- and Tissue-Specific Transcription in Transgenic Maize Plants," Plant Cell Physiol., vol. 41, No. 1, pp. 42-48, 2000.

Tingay, S. et al., "*Agrobacterium tumefaciens*-mediated barley transformation," The Plant Journal, vol. 11, No. 6, pp. 1369-1376, 1997.

Watson, B. et al., "Plasmid Required for Virulence of *Agrobacterium tumefaciens*," Journal of Bacteriology, vol. 123, No. 1, pp. 255-264, Jul. 1975.

Zhang, W. et al., "Cre/lox-mediated marker gene excision in transgenic maize (*Zea mays* L.) plants," Theor. Appl. Genet., vol. 107, pp. 1157-1168, 2003.

Zhao, Z.-Y. et al. "High throughput genetic transformation mediated by *Agrobacterium tumefaciens* in maize," Molecular Breeding, vol. 8, pp. 323-333, 2001.

Zhao, Z.-Y. et al., "*Agrobacterium*-mediated sorghum transformation," Plant Molecular Biology, vol. 44, pp. 789-798, 2000.

Frame et al., "Improved Agrobacterium-mediated transformation of three maize inbred lines using MS salts" Plant Cell Reports, vol. 25, (2006), pp. 1024-1034.

Trifonova et al., "Agrobacterium-mediated transgene delivery and intergration into barley under a range of in vitro culture conditions", Plant Science, vol. 161, (2001), pp. 871-880.

Hiei et al., "Improved protocols for transformation of indica rice mediated by Agrobacterium tumefaciens", Plant Cell, Tissue and Organ Culture, vol. 85, (2006), pp. 271-283.

\* cited by examiner

METHOD FOR INCREASING TRANSFORMATION EFFICIENCY IN PLANTS, COMPRISING COCULTURE STEP FOR CULTURING PLANT TISSUE WITH COCULTURE MEDIUM CONTAINING 3,6-DICHLORO-O-ANISIC ACID

The present application claims priority to Japanese Patent Application No. 2007-49161 filed on Feb. 28, 2007.

The present invention relates to a method for increasing Agrobacterium-mediated transformation efficiency in plants.

BACKGROUND ART

Methods previously known for transformation of monocotyledons such as maize and rice, which are major grain crops, include electroporation, particle gun transformation, etc. However, these physical gene transfer methods have problems in that genes are introduced as multiple copies or are not inserted in an intact state, and the resulting transformed plants may often develop malformations and sterility.

Agrobacterium-mediated gene transfer is universally used as a transformation method for dicotyledons. Although it has been understood that hosts of Agrobacterium are limited only to dicotyledons and Agrobacterium has no ability to infect monocotyledons (Non-patent Publication No. 1), some attempts have been made to transform monocotyledons through Agrobacterium-mediated method.

Grimsley et al. have reported that when maize streak virus DNA was inserted into T-DNA of Agrobacterium and inoculated into maize growing points, infection with maize streak virus was confirmed. Since such infection symptoms are not observed simply when the maize streak virus DNA alone is inoculated, Grimsley et al. have recognized that the above observation indicates the ability of Agrobacterium to introduce DNA into maize (Non-patent Publication No. 2). However, this result is not indicative of T-DNA integration into nuclei, because a virus will multiply even when not integrated into a nuclear genome. Grimsley et al. have further demonstrated that the highest infection efficiency is observed upon inoculation into a growing point in the shoot apex of maize (Non-patent Publication No. 3), and that the VirC gene in plasmids of Agrobacterium is essential for infection (Non-patent Publication No. 4).

Gould et al. injured maize growing points with a needle and then inoculated these growing points with super-virulent Agrobacterium EHA1 carrying the kanamycin resistance gene and the GUS gene, followed by kanamycin selection on the treated growing points to obtain a resistant plant. Upon Southern analysis to confirm whether progeny seeds of this plant have the introduced gene, they confirmed that some seeds had the transgene (Non-patent Publication No. 5). This indicates that the whole plant obtained by kanamycin selection on Agrobacterium-treated growing points had both transformed and non-transformed cells (chimerism).

Mooney et al. attempted to introduce the kanamycin resistance gene into wheat embryos by using Agrobacterium. First, the embryos were enzymatically treated to injure their cell walls, and then inoculated with Agrobacterium. Among the treated calli, very few calli were grown that appeared to be resistant to kanamycin, but no whole plant was regenerated from these calli. Upon Southern analysis to confirm the presence of the kanamycin resistance gene, all the resistant calli were found to have a structural mutation in the transgene (Non-patent Publication No. 6).

Raineri et al. performed super-virulent Agrobacterium A281 (pTiBo542) treatment on 8 varieties of rice whose embryonic disc had been injured, and they confirmed tumorous tissue growth in 2 varieties of Nipponbare, Fujisaka 5. Further, when rice embryos were inoculated with Agrobacterium carrying a Ti plasmid modified to have the kanamycin resistance gene and the GUS gene wherein hormone synthesis genes in T-DNA have been removed, the growth of kanamycin-resistant calli was observed. In these resistant calli, GUS gene expression was observed, but no transformed plant was obtained. Based on these results, Raineri et al. have recognized that the Agrobacterium T-DNA was introduced into rice cells (Non-patent Publication No. 7).

As shown above, there are study reports suggesting that Agrobacterium-mediated gene transfer is also possible for Gramineae crops including rice, maize and wheat, but these reports failed to show persuasive results because these studies had a problem in reproducibility and were also insufficient for transgene confirmation (Non-patent Publication No. 8).

Chan et al. injured immature rice embryos, which had been cultured for 2 days in the presence of 2,4-D, and then inoculated these embryos with Agrobacterium carrying genes for npt II and GUS in a medium containing suspension-cultured potato cells. They cultured the thus treated immature embryos on a G418-containing medium to obtain regenerated plants from the induced calli. They confirmed the location of the GUS gene in the regenerated plants and their progeny plants by Southern analysis, and reported that the presence of the transgene was observed in plants of both $R_0$ and $R_1$ generations (Non-patent Publication No. 9). This result supports Agrobacterium-mediated transformation in rice, but the transformation efficiency was as low as 1.6%. Moreover, there was only one regenerated plant that showed normal growth, although 250 immature embryos were used for testing. Since enormous efforts are required to extract immature embryos of rice, such low transformation efficiency is not practical.

In recent years, it has been reported that stable and highly efficient transformation is also possible in monocotyledons including rice and maize when using a super-binary vector carrying a part of the virulence gene from super-virulent Agrobacterium (Non-patent Documents 10 and 11). These reports suggest that Agrobacterium-mediated transformation not only allows stable and highly efficient transformation, but is also advantageous in that the resulting transformed plants have fewer mutations, and in that the introduced genes are low in copy number and are often in an intact state. Following success in rice and maize, further reports were issued for Agrobacterium-mediated transformation in other major grain crops, i.e., wheat (Non-patent Publication No. 12), barley (Non-patent Publication No. 13) and sorghum (Non-patent Publication No. 14).

Ishida et al. (1996) used maize inbred lines as materials to perform Agrobacterium-mediated transformation. Thereafter, further reports were issued for Agrobacterium-mediated transformation in maize (Non-patent Documents 15-21). Attempts which have been made to improve the efficiency of Agrobacterium-mediated maize transformation include: selection of transformed cells on N6 basal medium (Non-patent Publication No. 20); addition of $AgNO_3$ and carbenicillin to culture medium (Non-patent Publications 20 and 22); and addition of cysteine to coculture medium (Non-patent Publication No. 21). Ishida et al. (2003) (Non-patent Publication No. 22) have reported that the transformation efficiency in maize is improved when cocultured immature maize embryos are selected on a medium containing $AgNO_3$ and carbenicillin.

As shown above, in the case of Agrobacterium-mediated maize transformation, modifications to the medium composition or selection marker genes also result in improved efficiency and an extended range of varieties to be applied. However, the efficiency in maize remains at lower levels when compared to rice, which, like maize, is a monocotyledonous crop. Thus, the development of a method allowing more highly efficient transformation is desired, e.g. for test studies to determine the effects of isolated novel genes and/or for creation of a novel maize variety by gene recombination technology.

As in the case of 2,4-D (2,4-dichlorophenoxyacetic acid), dicamba (3,6-dichloro-o-anisic acid) is also used as a member of the plant hormone auxin during plant tissue culture. In maize tissue culture, dicamba is also used. Duncan et al. cultured maize immature embryos in a medium containing 4.5 µM 2,4-D or 15 µM dicamba, and reported that the formation rate of calli having regeneration ability was increased in the medium containing dicamba when compared to 2,4-D (Non-patent Publication No. 23). However, in almost all the cases recently reported for *Agrobacterium*-mediated maize transformation, immature embryos are cultured in a medium containing 2,4-D (Non-patent Documents 15-21, 24 and 25). Frame et al. performed *Agrobacterium*-mediated maize transformation in a medium containing 2,4-D or dicamba, and reported that the transformation efficiency was higher in the medium containing dicamba. However, in the media used for comparison by Frame et al., the 2,4-D concentration is 6.75 µM, whereas the dicamba concentration is 15 µM which is two or more times higher than that of 2,4-D. In addition to 2,4-D and dicamba, there are additional differences in the compositions of these media. Moreover, Frame et al. have discussed that the difference in transformation efficiency is due to a difference in the concentration of silver nitrate, which is higher in the dicamba-containing medium than in the 2,4-D-containing medium, and hence there is no information about effects resulting from a difference in the type of auxin (Non-patent Publication No. 26).

In view of the foregoing, the methods previously used in *Agrobacterium*-mediated maize transformation allow stable provision of transformed plants, but the transformation efficiency in maize is low when compared to rice, which is also a monocotyledonous crop. Thus, there has been a demand for the development of a method by which a transformant is obtained with higher efficiency.

Patent Publication No. 1: JP 2000-342255 A
Patent Publication No. 2: JP 2000-342256 A
Patent Publication No. 3: JP 2000-23675 A
Patent Publication No. 4: JP 2000-342253 A
Patent Publication No. 5: WO2005/017169
Patent Publication No. 6: WO2005/017152
Non-patent Publication No. 1: De Cleene, M. and De Ley, J. (1976) The host range of crown gall. Bot. Rev. 42:389-466.
Non-patent Publication No. 2: Grimsley, N., Horn, T., Davis, J. W. and Horn, B. (1987) *Agrobacterium*-mediated delivery of infectious maize streak virus into maize plants. Nature 325:177-179.
Non-patent Publication No. 3: Grimsley, N. H., Ramos, C., Hein, T. and Horn, B. (1988) Meristematic tissues of maize plants are most susceptible to Agroinfection with maize streak virus. Bio/technology 6:185-189.
Non-patent Publication No. 4: Grimsley, N., Horn, B., Ramos, C., Kado, C. and Rogowsky, P. (1989) DNA transfer from *Agrobacterium* to *Zea mays* or *Brassica* by agroinfection is dependent on bacterial virulence functions. Mol. Gen. Genet. 217:309-316.
Non-patent Publication No. 5: Gould, J., Devey, M., Hasegawa, O., Ulian, E. C., Peterson, G. and Smith, R. H. (1991) Transformation of *Zea mays* L. using *Agrobacterium tumefaciens* and shoot apex. Plant Physiol. 95:426-434.
Non-patent Publication No. 6: Mooney, P. A., Goodwin, P. B., Dennis, E. S. and Llewellyn, D. J. (1991) *Agrobacterium tumefaciens*-gene transfer into wheat tissues. Plant Cell, Tissues and Organ Culture 25:209-218.
Non-patent Publication No. 7: Raineri, D. M., Bottino, P., Gordon, M. P. and Nester, E. W. (1990) *Agrobacterium*-mediated transformation of rice (*Oryza sativa* L.). Bio/technology 8:33-38.
Non-patent Publication No. 8: Potrycus, I (1990) Gene transfer to cereals: an assessment. Bio/technology 8:535-542.
Non-patent Publication No. 9: Chan, M-T., Chang, H-H., Ho, S-L., Tong, W-F. and Yu, S-M. (1993) *Agrobacterium*-mediated production of transgenic rice plants expressing a chimeric α-amylase promoter/β-glucuronidase gene. Plant Mol. Biol. 22:491-506.
Non-patent Publication No. 10: Hici, Y., Ohta, S., Komari, T. and Kumashiro, T. (1994) Efficient transformation of rice (*Oryza sativa* L.) mediated by *Agrobacterium* and sequence analysis of the boundaries of the T-DNA. The Plant Journal 6:271-282.
Non-patent Publication No. 11: Ishida, Y., Saito, H., Ohta, S., Hici, Y., Komari, T. and Kumashiro, T. (1996) High efficiency transformation of maize (*Zea mays* L.) mediated by *Agrobacterium tumefaciens*. Nature Biotechnology 14:745-750.
Non-patent Publication No. 12: Cheng, M., Fry, J. E., Pang, S., Zhou, H., Hironaka, C. M., Duncan, D. R., Conner, T. W., Wan, Y. (1997) Genetic transformation of wheat mediated by *Agrobacterium tumefaciens*. Plant Physiol. 115: 971-980.
Non-patent Publication No. 13: Tingay, S., McElroy, D., Kalla, R., Fieg, S., Wang, M., Thornton, S., Brettell, R. (1997) *Agrobacterium tumefaciens*-mediated barley transformation. Plant J. 11: 1369-1376.
Non-patent Publication No. 14: Zhao, Z.-Y., Cai, T., Tagliani, L., Miller, M., Wang, N., Peng, H., Rudert, M., Schoeder, S., Hondred, D., Seltzer, J., Pierce, D. (2000) *Agrobacterium*-mediated sorghum transformation. Plant Mol. Biol. 44: 789-798.
Non-patent Publication No. 15: Deji, A., Sakakibara, H., Ishida, Y., Yamada, S., Komari, T., Kubo, T., Sugiyama, T. (2000) Genomic organization and transcriptional regulation of maize ZmRR1 and ZmRR2 encoding cytokinin-inducible response regulators. Biochim. et Biophys. Acta 1492: 216-220.
Non-patent Publication No. 16: Negrotto, D., Jolley, M., Beer, S., Wenck, A. R., Hansen, G. (2000) The use of phosphomannose-isomerase as a selection marker to recover transgenic maize plants (*Zea mays* L.) via *Agrobacterium* transformation. Plant Cell Reports 19: 798-803.
Non-patent Publication No. 17: Nomura, M., Sentoku, N., Nishimura, A., Lin, J-H., Honda, C., Taniguchi, M., Ishida, Y., Ohta, S., Komari, T., Miyao-Tokumori, M., Kono-Murakami, Y., Tajima, S., Ku, M. S. B., Matsuoka, M. (2000a) The evolution of C4 plants: acquisition of cis-regulatory sequences in the promoter of C4-type pyruvate, orthophosphate dikinase gene. Plant J. 22: 211-221.
Non-patent Publication No. 18: Nomura, M., Katayama, K., Nishimura, A., Ishida, Y., Ohta, S., Komari, T., Miyao-Tokutomi, M., Tajima, S., Matsuoka, M. (2000b) The promoter of rbcS in a C3 plant (rice) directs organ-specific, light-dependent expression in a C4 plant (maize), but does not confer bundle sheath cell-specific expression. Plant Mol. Biol. 44: 99-106.
Non-patent Publication No. 19: Taniguchi, M., Izawa, K., Ku, M. S. B., Lin, J-H., Saito, H., Ishida, Y., Ohta, S., Komari, T., Matsuoka, M., Sugiyama, T. (2000) The promoter for the maize $C_4$ pyruvate, orthophosphate dikinase gene directs cell- and tissue-specific transcription in transgenic maize plants. Plant Cell Physiol. 41: 42-48.

Non-patent Publication No. 20: Zhao, Z.-Y., Gu, W., Cai, T., Tagliani, L., Hondred, D., Bond, D., Schroeder, S., Rudert, M., Pierce, D. (2001) High throughput genetic transformation mediated by Agrobacterium tumefaciens in maize. Mol. Breed. 8: 323-333.

Non-patent Publication No. 21: Frame, B. R., Shou, H., Chikwamba, R. K., Zhang, Z., Xiang, C., Fonger, T. M., Pegg, S. E. K., Li, B., Nettleton, D. S., Pei, D., Wang, K. (2002) Agrobacterium tumefaciens-mediated transformation of maize embryos using a standard binary vector system. Plant Physiol. 129: 13-22.

Non-patent Publication No. 22: Ishida, Y., Saito, H., Hiei, Y., Komari, T. (2003) Improved protocol for transformation of maize (Zea mays L.) mediated by Agrobacterium tumefaciens. Plant Biotechnology 20:57-66.

Non-patent Publication No. 23: Duncan, D. R., Williams, M. E., Zehr, B. E., Widholm, J. M. (1985) The production of callus capable of plant regeneration from immature embryos of numerous Zea mays genotypes. Planta 165: 322-332.

Non-patent Publication No. 24: Zhang, W., Subbarao, S., Addae, P., Shen, A., Armstrong, C., Peschke, V., Gilbertson, L. (2003) Cre/lox-mediated marker gene excision in transgenic maize (Zea mays L.) plants. Theor. Appl. Genet. 107: 1157-1168.

Non-patent Publication No. 25: Huang, X. and Wei, Z. (2005) Successful Agrobacterium-mediated genetic transformation of maize elite inbred lines. Plant Cell, Tissue and Organ Culture 83:187-200.

Non-patent Publication No. 26: Frame, B. R., McMurray, J. M., Fonger, T. M., Main, M. L., Taylor, K. W., Torney, F. J., Paz, M. M., Wang, K. (2006) Improved Agrobacterium-mediated transformation of three maize inbred lines using MS salts. Plant Cell Rep. 25: 1024-1034.

Non-patent Publication No. 27: Komari, T., Hiei, Y., Saito, Y., Murai, N., Kumashiro, T. (1996) Vectors carrying two separate T-DNAs for co-transformation of higher plants mediated by Agrobacterium tumefaciens and segregation of transformants free from selection markers. The Plant Journal 10:165-174.

Non-patent Publication No. 28: Komari, T., Saito, Y., Nakakido, F., Kumashiro, T. (1989) Efficient selection of somatic hybrids in Nicotiana tabacum L. using a combination of drug-resistance merkers introduced by transformation. Theor. Appl. Genet. 77:547-552.

Non-patent Publication No. 29: Sambrook, J., Fritsch, E. F., Maniatis, T. (1989) Molecular Cloning: A Laboratory Manual, 2nd ed., Cold Spring Harbor Laboratory Press, Cold Spring Harbor, N.Y.

Non-patent Publication No. 30: Linsmaier, E., Skoog, F. (1965) Organic growth factor requirements of tobacco tissue culture. Physiol. Plant. 18:100-127.

Non-patent Publication No. 31: Chu, C.-C. (1978) The N6 medium and its applications to anther culture of cereal crops. In: Proc. Symp. Plant Tissue Culture. Peking: Science Press, pp 43-50.

Non-patent Publication No. 32: Watson, B., Currier, T. C., Gordon, M. P., Chilton, M.-D. and Nester, E. W. (1975) Plasmid required for virulence of Agrobacterium tumefaciens. J Bacteriol, 123, 255-264.

DISCLOSURE OF THE INVENTION

Problems to be Solved by the Invention

The object of the present invention is to provide a method for increasing transformation efficiency in plants when compared to conventionally known Agrobacterium-mediated methods.

Means for Solving the Problems

As a result of extensive and intensive efforts made to solve the problems stated above, the inventors of the present invention have found that by using a transformation method which comprises a coculture step for culturing an Agrobacterium-inoculated plant tissue with a coculture medium containing 3,6-dichloro-o-anisic acid (dicamba), the transformation efficiency in plants is increased when compared to conventional methods in which 2,4-dichlorophenoxyacetic acid (2,4-D) is used. This finding led to the completion of the present invention. The present invention is preferably accomplished by, but is not limited to, the embodiments shown below.

The present invention provides a method for increasing transformation efficiency in plants, which comprises a coculture step for culturing an Agrobacterium-inoculated plant tissue with a coculture medium containing 3,6-dichloro-o-anisic acid.

In a preferred embodiment of the present invention, the coculture medium is free from any auxin member other than 3,6-dichloro-o-anisic acid.

Moreover, in a preferred embodiment of the present invention, the concentration of 3,6-dichloro-o-anisic acid in the coculture medium is 0.5 to 3.0 mg/l.

Moreover, in a preferred embodiment of the present invention, the transformation efficiency in plants is increased 1.3-fold or more, more preferably 2.4-fold or more, when compared to the case where 2,4-dichlorophenoxyacetic acid alone is used as an auxin member in the coculture medium.

Moreover, in a preferred embodiment of the present invention, the plant tissue to be inoculated with Agrobacterium is derived from a monocotyledonous plant tissue. In a more preferred embodiment, the plant to be inoculated with Agrobacterium is maize, wheat or barley. The monocotyledonous plant tissue to be inoculated with Agrobacterium is an immature embryo, a callus, a flower bud or a germination site in a mature seed, and most preferably an immature embryo.

Further, in a preferred embodiment of the present invention, the plant tissue has been thermally-treated and/or centrifuged.

Moreover, in a preferred embodiment of the present invention, the coculture medium further comprises silver nitrate and/or copper sulfate.

In another embodiment, the present invention provides a method for producing a transformed plant, which comprises the following steps:

(i) a coculture step for culturing an Agrobacterium-inoculated plant tissue with a coculture medium containing 3,6-dichloro-o-anisic acid;

(ii) a selection step for culturing the tissue obtained in (i) with an auxin-containing medium to select a transformant by drug selection; and (iii) a regeneration step for culturing the tissue selected in (ii) with a regeneration medium containing a selective drug to thereby induce regeneration.

The constitution of the present invention will be described in more detail below.

The present invention provides a method for increasing transformation efficiency in plants, which comprises a coculture step for culturing an *Agrobacterium*-inoculated plant tissue with a coculture medium containing 3,6-dichloro-o-anisic acid.

*Agrobacterium*-mediated transformation of a plant tissue is generally accomplished by the following steps: (i) an inoculation step for inoculating *Agrobacterium* into the plant tissue; (ii) a coculture step for culturing the plant tissue with a coculture medium containing 2,4-dichlorophenoxyacetic acid (2,4-D); (iii) a selection step for culturing the plant tissue with a selective medium containing 2,4-D and a selective drug; and (iv) a regeneration step for culturing the plant tissue with a regeneration medium containing a selective drug.

In conventional transformation methods as shown above, 2,4-D is often used as an auxin member in the coculture step, and little attempt has been made to use another auxin member in place of 2,4-D or in combination with 2,4-D in a coculture medium. As used herein, the terms "auxin" and "auxin member" are intended to include both naturally occurring auxin and artificially synthesized auxin, which are known in the art. Examples include 2,4-D, dicamba, 4-amino-3,5,6-trichloropicolinic acid (picloram), 2,3,5-triiodobenzoic acid (TIBA), 2,4,5-trichlorophenoxyacetic acid (2,4,5-T), as well as indoleacetic acid (IAA), indolebutyric acid (IBA) and naphthaleneacetic acid (NAA), etc.

In the present invention, one of the features is to comprise 3,6-dichloro-o-anisic acid (dicamba) in the coculture medium, whereby the transformation efficiency in plants is increased. In a more preferred embodiment of the present invention, the coculture medium is free from any auxin member other than 3,6-dichloro-o-anisic acid (dicamba).

To determine whether a plant has been transformed or not, various known techniques may be used. For example, when a reporter gene (e.g., GUS (β-glucuronidase) gene, luciferase gene or GFP gene) is used as a gene to be transformed, the expression sites of these reporter genes may be visually confirmed for the presence or absence of transformation in a simple known manner. Alternatively, when using a selection marker gene such as an antibiotic resistance gene or a herbicide resistance gene, the development of resistance to the marker can be used as an indicator to confirm the presence or absence of transformation by culturing plant cells in a medium containing the antibiotic or herbicide or by treating a plant with a solution of the antibiotic or herbicide.

More accurate determination of whether a plant has been transformed or not may be accomplished, for example, by Southern hybridization technique for confirming integration of a transgene into the plant chromosome, and confirmation of transgene expression in progeny plants (inheritance to the progeny). Southern hybridization may be performed in a widely known manner, for example, as described in Molecular Cloning (Non-patent Publication No. 29). Likewise, the confirmation of transgene expression in progeny plants may be accomplished by any technique used for examining the expression of a reporter gene (e.g., GUS gene) or a selection marker gene (e.g., herbicide resistance gene), more specifically but not limited to, the technique described in Non-patent Publication No. 11.

Transformation efficiency can be determined by any calculation method commonly used by those skilled in the art, for example, can be determined from a value calculated by dividing the number of transformed plants by the number of *Agrobacterium*-inoculated explants.

In the present invention, "increasing transformation efficiency in plants" is intended to mean that the transformation efficiency is increased when compared to conventional *Agrobacterium*-mediated transformation methods in which 2,4-D alone is contained as auxin in a coculture medium, as shown above. When rising the method of the present invention, the transformation efficiency is increased 1.3-fold in Example 1 and 2.4-fold in Example 2, as compared to the method using 2,4-D. Thus, according to the present invention, the transformation efficiency is preferably increased 1.3-fold or more, more preferably 2.0-fold or more, and even more preferably 2.4-fold or more.

Explanation will be given below for each step in the method of the present invention for increasing transformation efficiency in plants.

(1) *Agrobacterium* Inoculation Step

The plant tissue used in the present invention is inoculated with *Agrobacterium*. The term "inoculation" or "inoculated" used herein is intended to mean that *Agrobacterium* is contacted with a plant tissue, and various techniques for *Agrobacterium* inoculation are known in the art. Examples of such techniques include those in which a plant tissue is added to a suspension of *Agrobacterium* suspended in a liquid medium, those in which an *Agrobacterium* suspension is directly added dropwise to a plant tissue on a coculture medium, those in which an *Agrobacterium* suspension is injected into a plant tissue, and those in which a plant tissue is immersed in an *Agrobacterium* suspension and incubated under reduced pressure. However, the *Agrobacterium*-inoculated plant tissue used in the present invention is not limited to those inoculated with *Agrobacterium* by these techniques.

In this *Agrobacterium* inoculation step, to improve the *Agrobacterium*-mediated transformation efficiency, for example, various additives (e.g., acetosyringone, surfactants, porous ceramics) may be incorporated into an *Agrobacterium* suspension.

*Agrobacterium* that can be used in the present invention may be any known *Agrobacterium*. Ln a preferred embodiment of the present invention, examples of *Agrobacterium* include, but are not limited to, LBA4404, EHA101 and AGL1, C58C1 and others. In a case where the vector used is not a super-binary vector (Non-patent Documents 10 and 11), it is preferable to use a strain carrying Ti plasmid pTiBo542 from *Agrobacterium* A281 (Non-patent Publication No. 31) in terms of transformation efficiency.

*Agrobacterium* is known to have the property of introducing a gene into the plant genome, wherein the gene has been inserted into T-DNA within a plasmid in the *Agrobacterium*. For this reason, *Agrobacterium* that can be used in the present invention has a plasmid in which a gene to be expressed is inserted into the T-DNA. Then, *Agrobacterium* having this plasmid may be inoculated into a plant tissue to achieve plant transformation, so that a preferred character is imparted to plant cells in the tissue. Examples of a plasmid for *Agrobacterium* that can be used in the present invention include, but are not limited to, pSB131, U0009B, U0017S, pSB134, pNB131 and pIG121Hm and others. In a case where the *Agrobacterium* strain used does not carry Ti plasmid pTiBo542, it is preferable to use a super-binary vector (Non-patent Documents 10 and 11) in terms of transformation efficiency.

The source plant of the plant tissue that can be used in the present invention may be either a monocotyledon or a dicotyledon, preferably a monocotyledon, more preferably maize, wheat or barley, and most preferably maize. Moreover, the plant tissue that can be used in the present invention may be, for example, a plant cell, a leaf, a root, a stem, a fruit, an immature embryo, a callus, a flower bud, a germination site in a mature seed, or a plant tissue of any other sites, preferably an immature embryo, a flower bud or a germination site in a mature seed, and most preferably an immature embryo. As used herein, the term "immature embryo" is intended to mean the embryo of an immature seed under maturation after pollination. The stage (maturation phase) of the immature embryo used in the method of the present invention is not limited in any way, and it may be collected at any stage after pollination. However, it is preferably at a post-pollination stage of 7 to 14 days.

To increase the transformation efficiency, such plant tissues as shown above may also be subjected to various treatments. Examples of such treatments include thermal treatment (Patent Publication No. 1), centrifugation (Patent Publication No. 2), thermal treatment and centrifugation (Patent Publication No. 4), as well as pressurization (Patent Publication No. 5).

(2) Coculture Step

In this step, plant cells inoculated with *Agrobacterium* as described above are cultured together with the *Agrobacterium* with a medium containing an auxin member to thereby ensure DNA introduction from the *Agrobacterium* into the plant cells. The medium used in this step is referred to herein as "coculture medium." The coculture medium may be any medium commonly used for plant cell culture, including those based on LS inorganic salts (Non-patent Publication No. 30) or N6 inorganic salts (Non-patent Publication No. 31), more specifically LS-AS medium.

According to conventional transformation methods, such a coculture medium is supplemented with 2,4-dichlorophenoxyacetic acid (2,4-D) as an auxin member. In the present invention, one of the features is to comprise 3,6-dichloro-o-anisic acid (dicamba) in the coculture medium. In a preferred embodiment of the present invention, the coculture medium is free from any auxin member other than dicamba.

The amount of dicamba in the coculture medium may be the same as that of 2,4-D in conventional methods, preferably 0.5 to 3.0 mg/l, more preferably 0.5 to 2.5 mg/l, even more preferably 1.0 to 2.0 mg/l, and most preferably 1.5 mg/l.

To increase the transformation efficiency, the coculture medium may further comprise various additives, in addition to dicamba. Examples of such additives include silver nitrate (Patent Publication No. 3), copper sulfate (Non-patent Publication No. 6), and cysteine (Non-patent Publication No. 21).

In this step, the coculture medium comprises dicamba as the only auxin member or comprises dicamba and other auxin member(s). Since auxin members generally have the ability to induce dedifferentiation in plant tissues, almost every plant tissue is partially or fully turned into a dedifferentiated tissue (callus) during this step and the subsequent selection step. The term "dedifferentiated tissue" or "callus" used herein is intended to mean a tissue obtained by culturing a part (explant) of a differentiated plant tissue with a medium containing a plant growth regulator such as auxin and cytokinin, wherein such a tissue is defined as an amorphous cell aggregate in an undifferentiated state which has lost the original form as a plant tissue. Thus, all embodiments involving such a dedifferentiated tissue fall within the scope of the present invention, including those where the coculture step is started with a dedifferentiated tissue, and those where a differentiated plant tissue fully or partially dedifferentiates during the coculture step or the subsequent selection step.

The term "culture" in this step is intended to mean that a plant tissue is placed on a solidified coculture medium or in a liquid coculture medium and is allowed to grow at an appropriate temperature under appropriate light/dark conditions for an appropriate period. The coculture medium may be solidified by addition of any solidifying agent known in the art, including agarose. The culture temperature in this step may be selected as appropriate, and is preferably 20° C. to 35° C., more preferably 25° C. Moreover, culture in this step is preferably accomplished in the dark, but is not limited thereto. The culture period in this step may also be selected as appropriate, and is preferably 1 to 10 days, more preferably 7 days.

(3) Selection Step

The present invention is characterized by comprising the coculture step described above. The selection step and regeneration step described below are commonly used in *Agrobacterium*-mediated plant transformation. The following description is therefore provided for illustrative purposes and is not intended to limit the present invention.

In this step, the tissue obtained in the above step is cultured with a medium containing an auxin member to select a transformant based on the presence or absence of gene transfer. The medium used in this step is referred to herein as "selective medium." Examples of a medium that can be used as a selective medium include those based on LS inorganic salts (Non-patent Publication No. 30) or N6 inorganic salts (Non-patent Publication No. 31), more specifically LSD1.5 medium. According to standard methods, such a selective medium is supplemented with an auxin member, preferably 2,4-D. Also in the present invention, the type of auxin member used in this selection step is not limited in any way, and preferred is 2,4-D. The selective medium may further comprise various additives, when required.

To select a transformed plant, for example, a plant after the above coculture step may be cultured with the selective medium containing an appropriate selective drug and then tested for the presence or absence of resistance to the selective drug. The selective drug that can be used in this step may be any drug commonly used in the art. For example, it is possible to use an antibiotic and/or a herbicide as a selective drug. Examples of an antibiotic available for use include hygromycin, kanamycin or blasticidin S. Likewise, examples of a herbicide available for use include phosphinothricin, bialaphos or glyphosate.

For this selection step, DNA inserted into T-DNA in *Agrobacterium* needs to comprise not only a gene to be expressed in a plant, but also, e.g., a resistance gene for a selective drug. Such a resistance gene for a selective drug is known in the art. In this step, for example, when a selective medium containing hygromycin is used for selection, the hygromycin resistance gene should be introduced from *Agrobacterium* into the plant.

Alternatively, a transformed plant may also be selected based on the sugar requirement of plant cells. Sugars assimilable by plant cells include sucrose, glucose and so on, but it is known that mannose cannot be assimilated. Thus, when cultured with a medium containing mannose as the only carbon source, plant tissues will die because there is no assimilable sugar. Selection based on sugar requirement relies on this principle. Namely, for use in this selection method, DNA inserted into T-DNA in *Agrobacterium* needs to comprise not only a gene to be expressed by a plant, but also a gene for phosphomannose isomerase (PMI). In this case, plant cells introduced with the PMI gene acquire the ability to assimilate mannose as a carbon source. Thus, only plant tissues transformed with such *Agrobacterium* as shown above can grow with a medium containing mannose as the only carbon source, whereby only transformed plant tissues can be selected (Non-patent Publication No. 16). Such a method is also possible for other sugars. For example, plant cells introduced with the xylose isomerase gene acquire the ability to assimilate xylose as a carbon source, and hence are applicable to such a method.

Thus, when a transformed plant is selected based on sugar requirement, a gene enabling the assimilation of sugars that are generally not assimilable by plant cells should be introduced from *Agrobacterium* into the plant tissue. Such a gene is known in the art and, for example, the PMI gene, the xylose isomerase gene or the like may be used for this purpose. Moreover, the selective medium should be prepared to exclude sucrose, glucose and other sugars, which are generally assimilable by plant cells and are generally contained in a medium. In place of these sugars, the selective medium contains only sugars which are not assimilable as carbon sources by normal plant cells. In this case, "sugars which are not assimilable by normal plant cells" are intended to mean sugars that cannot be used as nutrient sources because wild-type plant cells have no genes encoding metabolic enzymes for these sugars. Examples include mannose, xylose, etc.

Alternatively, an easily detectable gene may be introduced as a screening indicator to select a transformed plant based on the presence or absence of expression of this gene. Examples of such a gene serving as a screening indicator include the GFP gene, etc. Techniques to detect cells or tissues expressing these genes are known in the art. Selection may also be accomplished, e.g., by monitoring the expression site of such a gene as shown above and distinguishing this expression site.

This step may also be repeated for several rounds while varying the composition of medium components. For example, in the selection step repeated for several rounds, the selective drug concentration may be elevated at each round to ensure a higher reliability of drug selection, so that the possibility of obtaining a transformed whole plant can be increased. This selection step is preferably repeated for at least 2 rounds, more preferably 3 rounds. When the selection step is repeated for several rounds, a grown portion may be excised from the tissue cultured with a medium containing a selective drug, and this grown portion alone may then be provided for the next selection step, whereby a transformed tissue can be obtained efficiently.

The term "culture" in this step is intended to mean that a plant tissue is placed on a solidified selective medium or in a liquid selective medium and is allowed to grow at an appropriate temperature under appropriate light/dark conditions for an appropriate period. The selective medium may be solidified, for example, with agarose or the like as shown above. The culture temperature in this step may be selected as appropriate, and is preferably 20° C. to 35° C., more preferably 25° C. Moreover, culture in this step is preferably accomplished in the dark, but is not limited thereto. The culture period in this step may also be selected as appropriate. For example, when repeated for 3 rounds, the selection step is performed over 8 weeks in total, i.e., 2 weeks for first selection, 3 weeks for second selection, and 3 weeks for third selection. The total period for several rounds of selection is preferably 6 to 10 weeks, more preferably 7 to 9 weeks. Moreover, in several rounds of selection, the culture period, temperature and light/dark conditions can be varied in each round.

(4) Regeneration Step

In this step, the tissue selected in the above selection step is allowed to regenerate by being cultured with a medium. The medium used in this step is referred to herein as "regeneration medium." The regeneration medium contains no auxin member. Examples of a medium that can be used as a regeneration medium include those based on LS inorganic salts or N6 inorganic salts, more specifically LSZ medium.

In this step, the regeneration medium generally contains a selective drug. The selective drug that can be used in this step is as defined in the selection step. However, in this step, it is not always necessary to use the same selective drug as used in the selection step. In this case, resistance genes for two or more selective drugs should be introduced from *Agrobacterium* into the plant.

The term "regeneration" used herein is intended to mean that a fully or partially dedifferentiated plant tissue acquires again the properties of the original plant tissue or whole plant. In the present invention, dedifferentiation occurs in all or a part of almost every *Agrobacterium*-inoculated plant tissue by the action of auxin members during the coculture and selection steps. Thus, when subjected to this step, a dedifferentiated tissue will be able to regenerate, whereby a perfect transformed whole plant can be obtained.

The term "culture" in this step is intended to mean that a plant tissue is placed on a solidified regeneration medium or in a liquid regeneration medium and is allowed to grow at an appropriate temperature under appropriate light/dark conditions for an appropriate period. The regeneration medium may be solidified, for example, with agarose or the like as shown above. The culture temperature in this step may be selected as appropriate, and is preferably 20° C. to 35° C., more preferably 25° C. Moreover, culture in this step is preferably accomplished in the light for 16 to 24 hours a day, but is not limited thereto. The culture period in this step may also be selected as appropriate, and is preferably 7 to 21 days, more preferably 14 days.

After this step, a perfect transformed whole plant can be easily obtained in a manner known in the art. Thus, the present invention also provides a method for producing a transformed plant, which comprises the following steps:

(i) a coculture step for culturing an *Agrobacterium*-inoculated plant tissue with a coculture medium containing 3,6-dichloro-o-anisic acid;

(ii) a selection step for culturing the tissue obtained in (i) with an auxin-containing medium to select a transformant by drug selection; and (iii) a regeneration step for culturing the tissue selected in (ii) with a regeneration medium containing a selective drug to thereby induce regeneration.

ADVANTAGES OF THE INVENTION

The present invention achieved increased transformation efficiency in plants. This enables the efficient production of a transformed whole plant, and also allows a reduction in the cost required for obtaining such a whole plant.

Plasmid name: U0009B.prj

Plasmid size: 12347 bp

Figure 3:
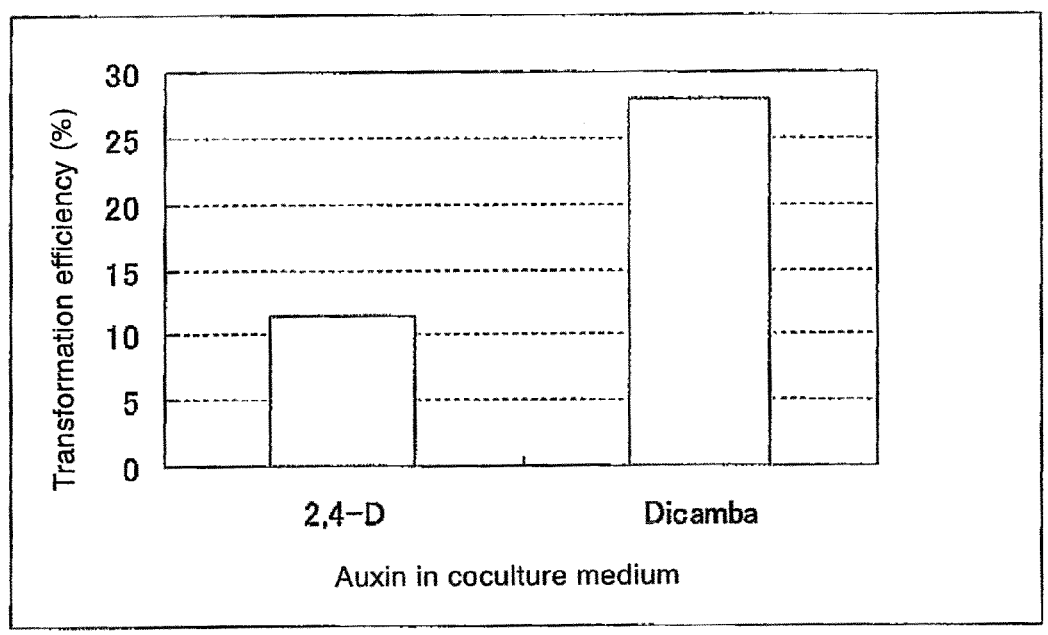

FIG. 3 is a graph showing the effect of auxin type in a coculture medium on transformation efficiency in maize (drop inoculation). 25 to 26 immature embryos were provided for each test. The vertical axis represents the transformation efficiency (calculated by dividing the number of GUS-positive plants obtained in each test by the number of inoculated immature embryos), while the horizontal axis represents the type of auxin contained in the coculture medium. The auxin concentration in the coculture medium was set to 1.5 mg/l for each test.

EXAMPLES

The present invention will now be further described by way of the following examples, which are provided for illustrative purposes only and are not intended to limit the present invention. The scope of the present invention is determined on the basis of the claims. Further, based on the detailed description, modifications and changes will be apparent to those skilled in the art.

Example 1

Effect of Coculture Medium Supplemented with Various Types of Auxin on Transformation Efficiency Material and Method Maize (variety: A188) immature embryos (1.0 to 1.5 mm in size) at 7 to 14 days after pollination were aseptically collected and washed once with LS-inf liquid medium (Non-patent Publication No. 11), followed by pretreatment (thermal treatment at 46° C. for 3 minutes and centrifugation at 15,000 rpm for 10 minutes) to increase gene transfer efficiency. In LS-inf liquid medium containing 100 μM acetosyringone, *Agrobacterium* strain LBA4404 (pSB131) (Non-patent Publication No. 11) was suspended at about $1.0 \times 10^9$ cfu/ml to prepare an inoculum. The thermally-treated and centrifuged immature embryos were mixed with the inoculum, vortexed for 30 seconds, and then allowed to stand for 5 minutes at room temperature. The *Agrobacterium*-inoculated immature embryos were placed, with their embryonic discs facing up, onto a coculture medium containing 2,4,5-T (2,4,5-trichlorophenoxyacetic acid), picloram (4-amino-3,5,6-trichloropicolinic acid), TIBA (2,3,5-triiodobenzoic acid) or dicamba at a concentration of 1.5 mg/l in LS-AS medium (Non-patent Publication No. 11; solidified with 8 g/l agarose) which had been prepared to exclude 2,4-D and contain 5 μM $AgNO_3$ and 5 μM $CuSO_4$. A control medium was prepared to contain 5 μM $AgNO_3$ and 5 μM $CuSO_4$ in LS-AS medium (solidified with 8 g/l agarose).

The immature embryos cultured in the dark at 25° C. for 7 days were placed onto LSD1.5 medium (Non-patent Publication No. 11) containing 5 μM $AgNO_3$, 5 mg/l phosphinothricin (PPT), 250 mg/l carbenicillin and 100 mg/l cefotaxime, and then cultured in the dark at 25° C. for 10 days. The immature embryos were transferred to the same medium, except that the PPT concentration was set to 10 mg/l, and cultured under the same conditions for 3 weeks. The grown calli were excised with a surgical knife, placed onto a fresh medium of the same composition, and cultured under the same conditions for 3 weeks. The grown calli were excised, placed onto LSZ medium (Non-patent Publication No. 11) containing 10 μM $CuSO_4$ and 5 mg/l PPT, and cultured in the light at 25° C. for about 2 weeks. Along with determining the number of immature embryos which regenerated into whole plants, leaves of the regenerated plants were partially excised, immersed in 0.1 M phosphate buffer (pH 6.8) containing 0.1% Triton X-100 and allowed to stand at 37° C. for 1 hour. The phosphate buffer was removed and then replaced with another phosphate buffer containing 1.0 mM 5-bromo-4-chloro-3-indolyl-β-D-glucuronic acid (X-gluc) and 20% methanol. After incubation at 37° C. for 24 hours, GUS gene expression was examined.

Results

Figure 1:
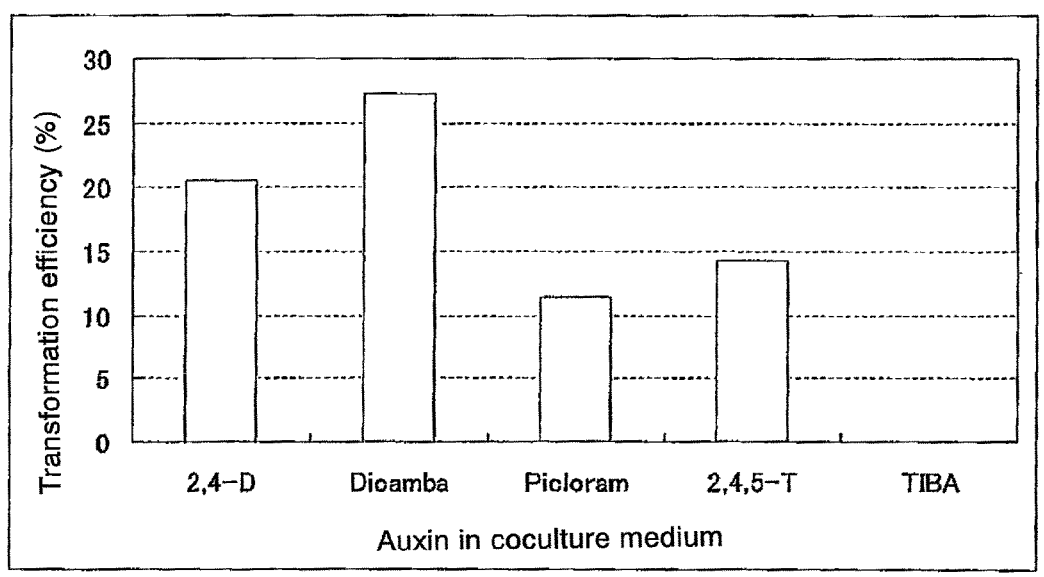
FIG. 1 is a graph showing the effect of auxin type in a coculture medium on transformation efficiency in maize. 33 to 35 immature embryos were provided for each test. The vertical axis represents the transformation efficiency (calculated by dividing the number of GUS-positive plants obtained in each test by the number of inoculated immature embryos), while the horizontal axis represents the type of auxin contained in the coculture medium. The auxin concentration in the coculture medium was set to 1.5 mg/l for each test.

From the immature embryos cultured on the control coculture medium containing 2,4-D as auxin, transformed plants were obtained with an efficiency of 20.6%. In contrast, the immature embryos cultured on the coculture medium containing dicamba as auxin were found to achieve a transformation efficiency as high as 27.3%, indicating that dicamba improved the transformation efficiency when used as auxin in a coculture medium. Thus, it was indicated that the incorporation of dicamba as auxin into a coculture medium caused a 1.33-fold 27.3/20.6) increase in the transformation efficiency, when compared to the conventional method using 2,4-D. On the other hand, the transformation efficiency in the medium containing 2,4,5-T or picloram as auxin was lower than that of the control. The immature embryos cocultured on the TIBA-containing medium produced no transformed plant (FIG. 1).

Example 2

Effect of Dicamba and 2,4-D in Coculture Medium on Transformation Efficiency (Drop Inoculation)

Material and Method

Figure 2:
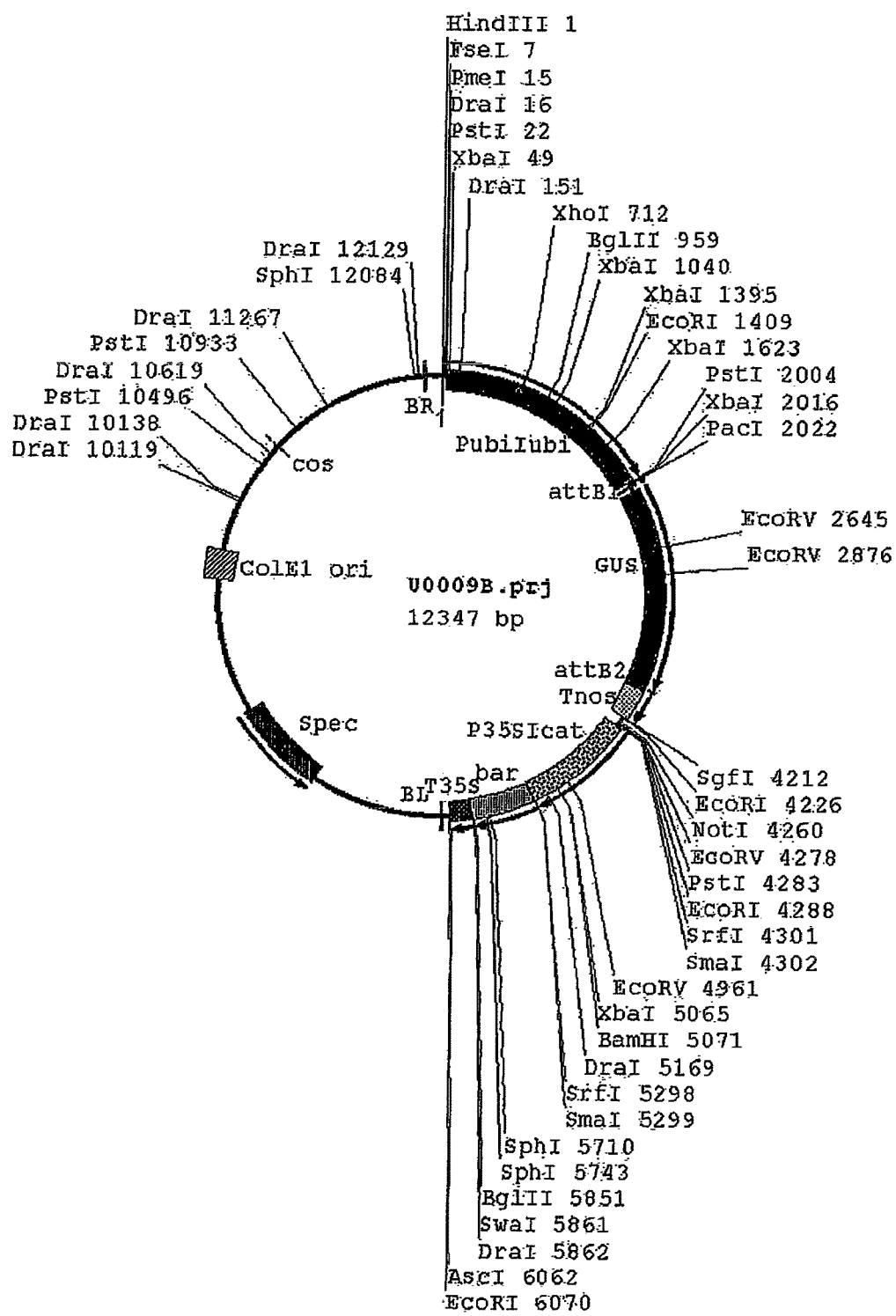
FIG. 2 shows the structure of plasmid U0009B from *Agrobacterium* strain LBA4404 (U0009B).

The vector U0009B shown in FIG. 2 and SEQ ID NO: 1 was constructed by adding necessary elements to a vector having pSB11 (Non-patent Publication No. 27) as a skeletal structure. An inoculum (1 ml) of *Agrobacterium* strain LBA4404 (U0009B) prepared in the same manner as shown in Example 1 was supplemented with about 80 mg of hydroxyapatite (Bio-Rad). After being pretreated (thermal treatment at 46° C. for 3 minutes and centrifugation at 15,000 rpm for 10 minutes) to increase gene transfer efficiency, immature embryos (variety: A188) were placed, with their embryonic discs facing up, onto a coculture medium containing dicamba at a concentration of 1.5 mg/l in LS-AS medium (Non-patent Publication No. 11; solidified with 8 g/l agarose) which had been prepared to exclude 2,4-D and contain 5 μM $AgNO_3$ and 5 μM $CuSO_4$. A control medium was prepared to contain 5 μM $AgNO_3$ and 5 μM $CuSO_4$ in LS-AS medium (solidified with 8 g/l agarose). After shaking with a vortex mixer to ensure a uniformly dispersed state of hydroxyapatite in the inoculum, 5 μl of the inoculum was added dropwise onto the immature embryos. After the inoculum added dropwise was dried, the immature embryos were transferred to another site on the same medium. After the culture container was sealed, coculture was performed in the dark at 25° C. for 7 days. The cocultured immature embryos were cultured in the same manner as shown in Example 1 to obtain regenerated plants, along with examining GUS gene expression in leaves of the regenerated plants.

Results

From the immature embryos cultured on the control coculture medium containing 2,4-D as auxin, transformed plants were obtained with an efficiency of 11.5%. In contrast, the immature embryos cultured on the coculture medium containing dicamba as auxin were found to achieve a transformation efficiency as high as 28.0%, indicating that dicamba also improved the transformation efficiency in the case of drop inoculation when used as auxin in a coculture medium (FIG. 3). According to this method, the addition of dicamba to a coculture medium caused a 2.43-fold (=28.0/11.5) increase in the transformation efficiency, when compared to the conventional method using 2,4-D.

Example 3

Southern Analysis

Material and Method

According to the method of Komari et al. (Non-patent Publication No. 28), DNAs were extracted from leaves of the transformed plants showing GUS gene expression obtained in Example 1. The extracted DNAs were each treated with a restriction enzyme BamHI, and subjected to Southern analysis using the GUS gene as a probe to detect the transgene. Southern analysis was performed as described in Molecular Cloning (Non-patent Publication No. 29).

Results

Each transformant showed a band hybridizing to the GUS probe. The band pattern differed from transformant to transformant, thus indicating that the transgene was randomly inserted onto the plant chromosome. The number of bands observed for the GUS-positive transformants was 1 to 3, and hence the copy number of the inserted transgene was found to be small in each case (Table 1).

TABLE 1

Copy number of GUS gene in transformed plants (T0)

| | Copy number of GUS gene | | |
|---|---|---|---|
| | 1 | 2 | 3 |
| Number of T0 plants | 11 | 2 | 2 |

The invention claimed is:

1. A method for increasing transformation efficiency in maize tissue comprising,
(i) a coculture step for culturing an *Agrobacterium*-inoculated maize tissue with a coculture medium containing 3,6-dichloro-o-anisic acid; and
(ii) a selection step for culturing the tissue obtained in (i) with a selection medium containing 2,4-dichlorophenoxyacetic acid (2,4-D).

2. The method according to claim 1, wherein the coculture medium is free from any auxin member other than 3,6-dichloro-o-anisic acid.

3. The method according to claim 1 or 2, wherein the concentration of 3,6-dichloro-o-anisic acid in the coculture medium is 0.5 to 3.0 mg/l.

4. The method according to claim 1, wherein the plant tissue has been thermally-treated and/or centrifuged.

5. The method according to claim 1, wherein the coculture medium further comprises silver nitrate and/or copper sulfate.

6. A method for producing a transformed maize plant, which comprises the following steps:
(i) a coculture step for culturing an *Agrobacterium*-inoculated maize tissue with a coculture medium containing 3,6-dichloro-o-anisic acid;
(ii) a selection step for culturing the tissue obtained in (i) with a selection medium containing 2,4-dichlorophenoxyacetic acid (2,4-D); and
(iii) a regeneration step for culturing the tissue selected in (ii) with a regeneration medium containing a selective drug to thereby induce regeneration.

* * * * *

SEQUENCE LISTING

```
<160> NUMBER OF SEQ ID NOS: 1

<210> SEQ ID NO 1
<211> LENGTH: 12347
<212> TYPE: DNA
<213> ORGANISM: Artificial
<220> FEATURE:
<223> OTHER INFORMATION: Plasmid for Agrobacterium

<400> SEQUENCE: 1
aagcttggcc ggccgtttaa actgcagcgt gacccggtcg tgcccctctc tagagataat    60
gagcattgca tgtctaagtt ataaaaaatt accacatatt tttttgtca cacttgtttg   120 aagtgcagtt tatctatctt tatacatata tttaaacttt actctacgaa taatataatc   180
tatagtacta caataaatac agtgttttag agaatcatat aaatgaacag ttagacatgg   240
tctaaaggac aattgagtat tttgacaaca ggactctaca gttttatctt tttagtgtgc   300
atgtgttctc cttttttttt gcaaatagct tcacctatat aatacttcat ccattttatt   360
agtacatcca tttagggttt agggttaatg gttttttatag actaattttt ttagtacatc   420
tattttattc tattttagcc tctaaattaa gaaaactaaa actctatttt agtttttta   480 tttaataatt tagatataaa atagaataaa ataaagtgac taaaaattaa acaaataccc   540
tttaagaaat taaaaaaact aaggaaacat ttttcttgtt tcgagtagat aatgccagcc   600
tgttaaacgc cgtcgacgag tctaacggac accaaccagc gaaccagcag cgtcgcgtcg   660
ggccaagcga agcagacggc acggcatctc tgtcgctgcc tctggacccc tctcgagagt   720
tccgctccac cgttggactt gctccgctgt cggcatccaa aaattgcgtg gcggagcggc   780
agacgtgagc cggcacggca ggcggcctcc tcctcctctc acggcaccgg cagctacggg   840
ggattccttt cccaccgctc cttcgctttc ccttcctcgc ccgccgtaat aaatagacac   900
cccctccaca ccctctttcc ccaacctcgt gttgttcgga gcgcacacac acacaaccag   960
atctccccca aatccacccg tcggcacctc cgcttcaagg tacgccgctc gtcctccccc  1020
cccccccctc tctaccttct ctagatcggc gttccggtcc atggttaggg cccggtagtt  1080
ctacttctgt tcatgtttgt gttagatccg tgtttgtgtt agatccgtgc tgctagcgtt  1140
cgtacacgga tgcgacctgt acgtcagaca cgttctgatt gctaacttgc cagtgtttct  1200
cttttgggaa tcctgggatg gctctagccg ttccgcagac gggatcgatt tcatgatttt  1260
ttttgtttcg ttgcataggg tttggtttgc ccttttcctt tatttcaata tatgccgtgc  1320
acttgtttgt cgggtcatct tttcatgctt ttttttgtct tggttgtgat gatgtggtct  1380
```

```
ggttgggcgg tcgttctaga tcggagtaga attctgtttc aaactacctg gtggatttat    1440
taattttgga tctgtatgtg tgtgccatac atattcatag ttacgaattg aagatgatgg    1500
atggaaatat cgatctagga taggtataca tgttgatgcg ggttttactg atgcatatac    1560
agagatgctt tttgttcgct tggttgtgat gatgtggtgt ggttgggcgg tcgttcattc    1620
gttctagatc ggagtagaat actgtttcaa actacctggt gtatttatta attttggaac    1680
tgtatgtgtg tgtcatacat cttcatagtt acgagtttaa gatggatgga aatatcgatc    1740
taggataggt atacatgttg atgtgggttt tactgatgca tatacatgat ggcatatgca    1800
gcatctattc atatgctcta accttgagta cctatctatt ataataaaca agtatgtttt    1860
ataattattt tgatcttgat atacttggat gatggcatat gcagcagcta tatgtggatt    1920
tttttagccc tgccttcata cgctatttat ttgcttggta ctgtttcttt tgtcgatgct    1980
caccctgttg tttggtgtta cttctgcagg tcgactctag attaattaag ttatcacaag    2040
tttgtacaaa aaagcaggct catttaactt taagaaggag atatatacca tggtccgtcc    2100
tgtagaaacc ccaacccgtg aaatcaaaaa actcgacggc ctgtgggcat tcagtctgga    2160
tcgcgaaaac tgtggaattg atcagcgttg gtgggaaagc gcgttacaag aaagccgggc    2220
aattgctgtg ccaggcagtt ttaacgatca gttcgccgat gcagatattc gtaattatgc    2280
gggcaacgtc tggtatcagc gcgaagtctt tataccgaaa ggttgggcag ccagcgtat    2340 cgtgctgcgt ttcgatgcgg tcactcatta cggcaaagtg tgggtcaata atcaggaagt    2400
gatggagcat cagggcggct atacgccatt tgaagccgat gtcacgccgt atgttattgc    2460
cgggaaaagt gtacgtatca ccgtttgtgt gaacaacgaa ctgaactggc agactatccc    2520
gccgggaatg gtgattaccg acgaaaacgg caagaaaaag cagtcttact tccatgattt    2580
ctttaactat gccggaatcc atcgcagcgt aatgctctac accacgccga cacctgggt    2640 ggacgatatc accgtggtga cgcatgtcgc gcaagactgt aaccacgcgt ctgttgactg    2700
gcaggtggtg gccaatggtg atgtcagcgt tgaactgcgt gatgcggatc aacaggtggt    2760
tgcaactgga caaggcacta gcgggacttt gcaagtggtg aatccgcacc tctggcaacc    2820
gggtgaaggt tatctctatg aactgtgcgt cacagccaaa agccagacag agtgtgatat    2880
ctacccgctt cgcgtcggca tccggtcagt ggcagtgaag ggcgaacagt tcctgattaa    2940
ccacaaaccg ttctacttta ctggctttgg tcgtcatgaa gatgcggact acgtggcaa    3000 aggattcgat aacgtgctga tggtgcacga ccacgcatta atggactgga ttggggccaa    3060
ctcctaccgt acctcgcatt acccttacgc tgaagagatg ctcgactggg cagatgaaca    3120
tggcatcgtg gtgattgatg aaactgctgc tgtcggcttt aacctctctt taggcattgg    3180
tttcgaagcg ggcaacaagc cgaaagaact gtacagcgaa gaggcagtca acggggaaac    3240
tcagcaagcg cacttacagg cgattaaaga gctgatagcg cgtgacaaaa accacccaag    3300
cgtggtgatg tggagtattg ccaacgaacc ggatacccgt ccgcaaggtg cacgggaata    3360
tttcgcgcca ctggcggaag caacgcgtaa actcgacccg acgcgtccga tcacctgcgt    3420
caatgtaatg ttctgcgacg ctcacaccga taccatcagc gatctctttg atgtgctgtg    3480
cctgaaccgt tattacgat ggtatgtcca aagcggcgat ttggaaacgg cagagaaggt    3540
actggaaaaa gaacttctgg cctggcagga gaaactgcat cagccgatta tcatcaccga    3600
atacggcgtg gatacgttag ccgggctgca ctcaatgtac accgacatgt ggagtgaaga    3660
gtatcagtgt gcatggctgg atatgtatca ccgcgtcttt gatcgcgtca gcgccgtcgt    3720
cggtgaacag gtatggaatt cgccgattt tgcgacctcg caaggcatat gcgcgttgg    3780
```

```
cggtaacaag aaagggatct tcactcgcga ccgcaaaccg aagtcggcgg cttttctgct   3840
gcaaaaacgc tggactggca tgaacttcgg tgaaaaaccg cagcagggag gcaaacaata   3900
atacccagct ttcttgtaca aagtggtgat aacagatcgt tcaaacattt ggcaataaag   3960
tttcttaaga ttgaatcctg ttgccggtct tgcgatgatt atcatataat ttctgttgaa   4020
ttacgttaag catgtaataa ttaacatgta atgcatgacg ttatttatga gatgggtttt   4080
tatgattaga gtcccgcaat tatacattta atacgcgata gaaaacaaaa tatagcgcgc   4140
aaactaggat aaattatcgc gcgcggtgtc atctatgtta ctagatccga tgataagctg   4200
tcaaacatga ggcgatcgca agggcgaatt ccagcacact ggcggccgtt actagtcgag   4260
cggccgccag tgtgatggat atctgcagaa ttcgcccttc gcccgggccc cgagcaataa   4320
tctccaggag atcaaatacc ttcccaagaa ggttaaagat gcagtcaaaa gattcaggac   4380
taactgcatc aagaacacag agaaagatat atttctcaag atcagaagta ctattccagt   4440
atggacgatt caaggcttgc ttcacaaacc aaggcaagta atagagattg gagtctctaa   4500
aaaggtagtt cccactgaat caaaggccat ggagtcaaag attcaaatag aggacctaac   4560
agaactcgcc gtaaagactg gcgaacagtt catacagagt ctcttacgac tcaatgacaa   4620
gaagaaaatc ttcgtcaaca tggtggagca cgacacgctt gtctactcca aaaatatcaa   4680
agatacagtc tcagaagacc aaagggcaat tgagactttt caacaaaggg taatatccgg   4740
aaacctcctc ggattccatt gcccagctat ctgtcacttt attgtgaaga tagtggaaaa   4800
ggaaggtggc tcctacaaat gccatcattg cgataaagga aaggccatcg ttgaagatgc   4860
ctctgccgac agtggtccca agatggaccc cccacccacg aggagcatcg tggaaaaaga   4920
agacgttcca accacgtctt caaagcaagt ggattgatgt gatatctcca ctgacgtaag   4980
ggatgacgca caatcccact atccttcgca agacccttcc tctatataag gaagttcatt   5040
tcatttggag aggacacggg ggactctaga ggatccccga tccctacagg gtaaatttct   5100
agtttttctc cttcattttc ttggttagga ccctttttctc ttttttatttt tttgagcttt   5160
gatctttctt taaactgatc tattttttaa ttgattggtt atggtgtaaa tattacatag   5220
ctttaactga taatctgatt actttatttc gtgtgtctat gatgatgatg atagttacag   5280
aaccgtcgag ggggatcgcc cgggccatgg acccagaacg acgcccggcc gacatccgcc   5340
gtgccaccga ggcggacatg ccggcggtct gcaccatcgt caaccactac atcgagacaa   5400
gcacggtcaa cttccgtacc gagccgcagg aaccgcagga gtggacggac gacctcgtcc   5460
gtctgcggga gcgctatccc tggctcgtcg ccgaggtgga cggcgaggtc gccggcatcg   5520
cctacgcggg ccccctggaag gcacgcaacg cctacgactg gacggccgag tcgaccgtgt   5580
acgtctcccc ccgccaccag cggacgggac tgggctccac gctctacacc cacctgctga   5640
agtccctgga ggcacagggc ttcaagagcg tggtcgctgt catcgggctg cccaacgacc   5700
cgagcgtgcg catgcacgag gcgctcggat atgcccccg cggcatgctg cggcggccg   5760
gcttcaagca cgggaactgg catgacgtgg gtttctggca gctggacttc agcctgccgg   5820
taccgccccg tccggtcctg cccgtcaccg agatctgatc atttaaattg aaatcaccag   5880
tctctctcta caaatctatc tctctctata ataatgtgtg agtagttccc agataaggga   5940
attagggttc ttatagggtt tcgctcatgt gttgagcata taagaaaccc ttagtatgta   6000
tttgtatttg taaaatactt ctatcaataa aatttctaat tcctaaaacc aaaatccagt   6060
gggcgcgcca aattcagtac attaaaaacg tccgcaatgt gttattaagt tgtctaagcg   6120
tcaatttgtt tacaccacaa tatatcctgc caccagccag ccaacagctc cccgaccggc   6180
```

```
agctcggcac aaaatcacca ctcgatacag gcagcccatc agtccgggac ggcgtcagcg    6240
ggagagccgt tgtaaggcgg cagactttgc tcatgttacc gatgctattc ggaagaacgg    6300
caactaagct gccgggtttg aaacacggat gatctcgcgg agggtagcat gttgattgta    6360
acgatgacag agcgttgctg cctgtgatca aatatcatct ccctcgcaga gatccgaatt    6420
atcagccttc ttattcattt ctcgcttaac cgtgacaggc tgtcgatctt gagaactatg    6480
ccgacataat aggaaatcgc tggataaagc cgctgaggaa gctgagtggc gctatttctt    6540
tagaagtgaa cgttgacgat cgtcgaccgt accccgatga attaattcgg acgtacgttc    6600
tgaacacagc tggatactta cttgggcgat tgtcatacat gacatcaaca atgtacccgt    6660
ttgtgtaacc gtctcttgga ggttcgtatg acactagtgg ttcccctcag cttgcgacta    6720
gatgttgagg cctaacattt tattagagag caggctagtt gcttagatac atgatcttca    6780
ggccgttatc tgtcagggca agcgaaaatt ggccatttat gacgaccaat gccccgcaga    6840
agctcccatc tttgccgcca tagacgccgc gccccccttt tggggtgtag aacatccttt    6900
tgccagatgt ggaaaagaag ttcgttgtcc cattgttggc aatgacgtag tagccggcga    6960
aagtgcgaga cccatttgcg ctatatataa gcctacgatt tccgttgcga ctattgtcgt    7020
aattggatga actattatcg tagttgctct cagagttgtc gtaatttgat ggactattgt    7080
cgtaattgct tatggagttg tcgtagttgc ttggagaaat gtcgtagttg gatggggagt    7140
agtcataggg aagacgagct tcatccacta aaacaattgg caggtcagca agtgcctgcc    7200
ccgatgccat cgcaagtacg aggcttagaa ccaccttcaa cagatcgcgc atagtcttcc    7260
ccagctctct aacgcttgag ttaagccgcg ccgcgaagcg gcgtcggctt gaacgaattg    7320
ttagacatta tttgccgact accttggtga tctcgccttt cacgtagtga acaaattctt    7380
ccaactgatc tgcgcgcgag gccaagcgat cttcttgtcc aagataagcc tgcctagctt    7440
caagtatgac gggctgatac tgggccggca ggcgctccat tgcccagtcg gcagcgacat    7500
ccttcggcgc gattttgccg gttactgcgc tgtaccaaat gcgggacaac gtaagcacta    7560
catttcgctc atcgccagcc cagtcgggcg gcgagttcca tagcgttaag gtttcattta    7620
gcgcctcaaa tagatcctgt tcaggaaccg gatcaaagag ttcctccgcc gctggaccta    7680
ccaaggcaac gctatgttct cttgcttttg tcagcaagat agccagatca atgtcgatcg    7740
tggctggctc gaagatacct gcaagaatgt cattgcgctg ccattctcca aattgcagtt    7800
cgcgcttagc tggataacgc cacggaatga tgtcgtcgtg cacaacaatg gtgacttcta    7860
cagcgcggag aatctcgctc tctccagggg aagccgaagt ttccaaaagg tcgttgatca    7920
aagctcgccg cgttgtttca tcaagcctta cggtcaccgt aaccagcaaa tcaatatcac    7980
tgtgtggctt caggccgcca tccactgcgg agccgtacaa atgtacggcc agcaacgtcg    8040
gttcgagatg gcgctcgatg acgccaacta cctctgatag ttgagtcgat acttcggcga    8100
tcaccgcttc cctcatgatg tttaactcct gaattaagcc gcgccgcgaa gcggtgtcgg    8160
cttgaatgaa ttgttaggcg tcatcctgtg ctcccgagaa ccagtaccag tacatcgctg    8220
tttcgttcga gacttgaggt ctagttttat acgtgaacag gtcaatgccg ccgagagtaa    8280
agccacattt tgcgtacaaa ttgcaggcag gtacattgtt cgtttgtgtc tctaatcgta    8340
tgccaaggag ctgtctgctt agtgcccact ttttcgcaaa ttcgatgaga ctgtgcgcga    8400
ctcctttgcc tcggtgcgtg tgcgacacaa caatgtgttc gatagaggct agatcgttcc    8460
atgttgagtt gagttcaatc ttcccgacaa gctcttggtc gatgaatgcg ccatagcaag    8520
cagagtcttc atcagagtca tcatccgaga tgtaatcctt ccggtagggg ctcacacttc    8580
```

```
tggtagatag ttcaaagcct tggtcggata ggtgcacatc gaacacttca cgaacaatga    8640
aatggttctc agcatccaat gtttccgcca cctgctcagg gatcaccgaa atcttcatat    8700
gacgcctaac gcctggcaca gcggatcgca aacctggcgc ggctttgggc acaaaaggcg    8760
tgacaggttt gcgaatccgt tgctgccact tgttaaccct tttgccagat ttggtaacta    8820
taatttatgt tagaggcgaa gtcttgggta aaaactggcc taaaattgct ggggatttca    8880
ggaaagtaaa catcaccttc cggctcgatg tctattgtag atatatgtag tgtatctact    8940
tgatcggggg atctgctgcc tcgcgcgttt cggtgatgac ggtgaaaacc tctgacacat    9000
gcagctcccg gagacggtca cagcttgtct gtaagcggat gccgggagca gacaagcccg    9060
tcagggcgcg tcagcgggtg ttggcgggtg tcggggcgca gccatgaccc agtcacgtag    9120
cgatagcgga gtgtatactg gcttaactat gcggcatcag agcagattgt actgagagtg    9180
caccatatgc ggtgtgaaat accgcacaga tgcgtaagga gaaaataccg catcaggcgc    9240
tcttccgctt cctcgctcac tgactcgctg cgctcggtcg ttcggctgcg gcgagcggta    9300
tcagctcact caaaggcggt aatacggtta tccacagaat caggggataa cgcaggaaag    9360
aacatgtgag caaaaggcca gcaaaaggcc aggaaccgta aaaaggccgc gttgctggcg    9420 ttttccata ggctccgccc ccctgacgag catcacaaaa atcgacgctc aagtcagagg    9480
tggcgaaacc cgacaggact ataaagatac caggcgtttc cccctggaag ctccctcgtg    9540
cgctctcctg ttccgaccct gccgcttacc ggatacctgt ccgcctttct cccttcggga    9600
agcgtggcgc tttctcatag ctcacgctgt aggtatctca gttcggtgta ggtcgttcgc    9660
tccaagctgg gctgtgtgca cgaaccccc gttcagcccg accgctgcgc cttatccggt    9720
aactatcgtc ttgagtccaa cccggtaaga cacgacttat cgccactggc agcagccact    9780
ggtaacagga ttagcagagc gaggtatgta ggcggtgcta cagagttctt gaagtggtgg    9840
cctaactacg gctacactag aaggacagta tttggtatct gcgctctgct gaagccagtt    9900
accttcggaa aaagagttgg tagctcttga tccggcaaac aaaccaccgc tggtagcggt    9960
ggtttttttg tttgcaagca gcagattacg cgcagaaaaa aaggatctca agaagatcct   10020
ttgatctttt ctacggggtc tgacgctcag tggaacgaaa actcacgtta agggattttg   10080
gtcatgagat tatcaaaaag gatcttcacc tagatccttt taaattaaaa atgaagtttt   10140
aaatcaatct aaagtatata tgagtaaact tggtctgaca gttaccaatg cttaatcagt   10200
gaggcaccta tctcagcgat ctgtctattt cgttcatcca tagttgcctg actccccgtc   10260
gtgtagataa ctacgatacg ggagggctta ccatctggcc ccagtgctgc aatgataccg   10320
cgagacccac gctcaccggc tccagattta tcagcaataa accagccagc cggaagggcc   10380
gagcgcagaa gtggtcctgc aactttatcc gcctccatcc agtctattaa ttgttgccgg   10440
gaagctagag taagtagttc gccagttaat agtttgcgca acgttgttgc cattgctgca   10500 ggggggggg ggggggggtt ccattgttca ttccacggac aaaaacagag aaaggaaacg   10560
acagaggcca aaaagctcgc tttcagcacc tgtcgtttcc tttcttttca gagggtattt   10620
taaataaaaa cattaagtta tgacgaagaa gaacggaaac gccttaaacc ggaaaatttt   10680
cataaatagc gaaaacccgc gaggtcgccg ccccgtaacc tgtcggatca ccggaaagga   10740
cccgtaaagt gataatgatt atcatctaca tatcacaacg tgcgtggagg ccatcaaacc   10800
acgtcaaata atcaattatg acgcaggtat cgtattaatt gatctgcatc aacttaacgt   10860
aaaaacaact tcagacaata caaatcagcg acactgaata cggggcaacc tcatgtcccc   10920 ccccccccc cctgcaggc atcgtggtgt cacgctcgtc gtttggtatg gcttcattca   10980
```

-continued

```
gctccggttc ccaacgatca aggcgagtta catgatcccc catgttgtgc aaaaaagcgg    11040
ttagctcctt cggtcctccg atcgttgtca gaagtaagtt ggccgcagtg ttatcactca    11100
tggttatggc agcactgcat aattctctta ctgtcatgcc atccgtaaga tgcttttctg    11160
tgactggtga gtactcaacc aagtcattct gagaatagtg tatgcggcga ccgagttgct    11220
cttgcccggc gtcaacacgg gataataccg cgccacatag cagaacttta aaagtgctca    11280
tcattggaaa acgttcttcg gggcgaaaac tctcaaggat cttaccgctg ttgagatcca    11340
gttcgatgta acccactcgt gcacccaact gatcttcagc atcttttact ttcaccagcg    11400
tttctgggtg agcaaaaaca ggaaggcaaa atgccgcaaa aaagggaata agggcgacac    11460
ggaaatgttg aatactcata ctcttccttt ttcaatatta ttgaagcatt tatcagggtt    11520
attgtctcat gagcggatac atatttgaat gtatttagaa aaataaacaa ataggggttc    11580
cgcgcacatt tccccgaaaa gtgccacctg acgtctaaga aaccattatt atcatgacat    11640
taacctataa aataggcgt atcacgaggc cctttcgtct tcaagaattg gtcgacgatc    11700
ttgctgcgtt cggatatttt cgtggagttc ccgccacaga cccggattga aggcgagatc    11760
cagcaactcg cgccagatca tcctgtgacg gaactttggc gcgtgatgac tggccaggac    11820
gtcggccgaa agagcgacaa gcagatcacg cttttcgaca gcgtcggatt tgcgatcgag    11880 gattttcgg cgctgcgcta cgtccgcgac cgcgttgagg gatcaagcca cagcagccca    11940
ctcgaccttc tagccgaccc agacgagcca agggatcttt ttggaatgct gctccgtcgt    12000
caggctttcc gacgtttggg tggttgaaca gaagtcatta tcgcacggaa tgccaagcac    12060
tcccgagggg aaccctgtgg ttggcatgca catacaaatg gacgaacgga taaacctttt    12120
cacgcccttt taaatatccg attattctaa taaacgctct tttctcttag gtttaccgc    12180 caatatatcc tgtcaaacac tgatagttta acctgaaggc gggaaacgac aatctgatca    12240
tgagcggaga attaagggag tcacgttatg accccgccg atgacgcggg acaagccgtt    12300
ttacgtttgg aactgacaga accgcaacgt tgaaggagcc actcagc              12347
```